US005663167A

United States Patent [19]
Pickar et al.

[11] Patent Number: 5,663,167
[45] Date of Patent: *Sep. 2, 1997

[54] ANTIPSYCHOTIC COMPOSITION AND METHOD OF TREATMENT

[75] Inventors: David Pickar; Robert E. Litman, both of Bethesda, Md.; William Z. Potter, Washington, D.C.

[73] Assignee: The United States of America as represented by the Department of Health and Human Services, Washington, D.C.

[*] Notice: The term of this patent shall not extend beyond the expiration date of Pat. No. 5,492,907.

[21] Appl. No.: 479,039

[22] Filed: Jun. 7, 1995

Related U.S. Application Data

[63] Continuation-in-part of Ser. No. 987,728, Dec. 9, 1992, Pat. No. 5,492,907.
[51] Int. Cl.⁶ .................................................. A61K 31/54
[52] U.S. Cl. .................. 514/225.8; 514/211; 514/215; 514/220; 514/224.8; 514/225.5; 514/226.2; 514/235.2; 514/280; 514/341; 514/397; 514/401; 514/402; 514/422; 514/253
[58] Field of Search .................... 514/225.8, 211, 514/215, 220, 224.8, 225.5, 226.2, 235.2, 280, 341, 397, 401, 402, 422, 253

[56] References Cited

U.S. PATENT DOCUMENTS

| | | | |
|---|---|---|---|
| 4,138,484 | 2/1979 | Fuxe | 424/247 |
| 4,508,715 | 4/1985 | Booth | 424/246 |
| 4,851,416 | 7/1989 | Vizi | 514/280 |
| 5,015,654 | 5/1991 | Al-Damluji | 514/402 |
| 5,492,907 | 2/1996 | Picker | 514/225.8 |

OTHER PUBLICATIONS

"The Merck Manual of Diagnosis and Therapy," 14$^{th}$ Ed., pp. 1462–1468 (1982).

Gordon, "Psychopharmacological Agents," vol. 1, pp. 28–34 (1964).

Litman, 1992 Abstracts of Panels and Poster, Am. Coll. Neuropsychopharmacology, 30th Ann. Mtg., Dec. 9–13 1991, Poster Session II. p. 164.

Kane, Arch. Gen. Psychiatry, 45, pp. 789–796 (1988).

Doxey, Arch. Pharmacol., 325, pp. 136–144 (1984).

*Primary Examiner*—Michael L. Shippen
*Attorney, Agent, or Firm*—Foley & Lardner

[57] ABSTRACT

A method for treating a serious psychotic mental illness includes the step of administering to a patient in need of such treatment a combination of (i) an $\alpha_2$-adrenergic receptor antagonist and (ii) a $D_2$ dopamine receptor antagonist. A pharmaceutical composition useful in the novel method includes an effective amount of the combination of the foregoing two ingredients together with a pharmaceutically acceptable carrier.

15 Claims, 2 Drawing Sheets

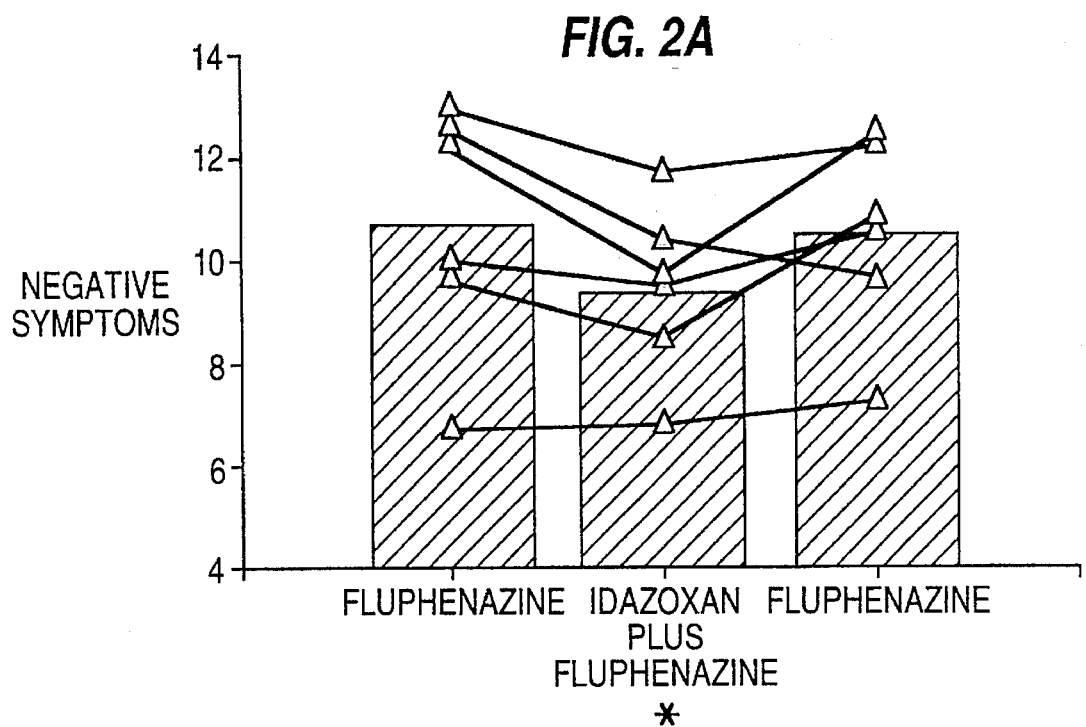
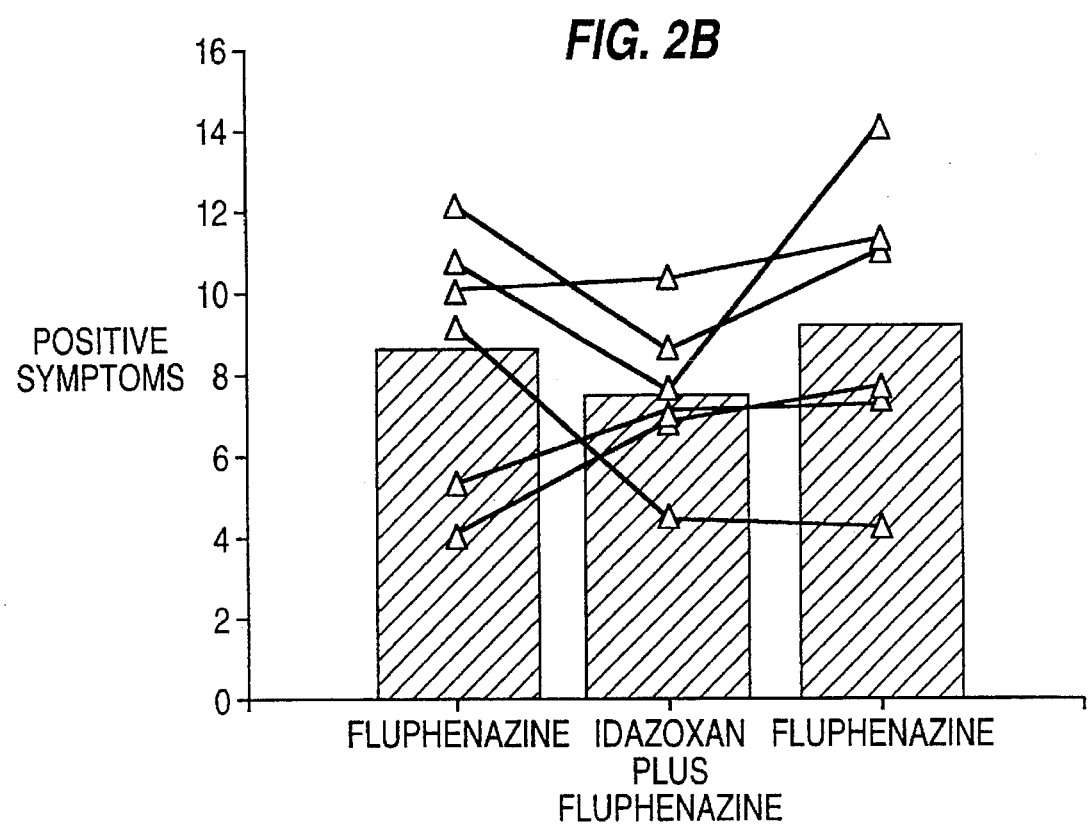

ANTIPSYCHOTIC COMPOSITION AND METHOD OF TREATMENT

REFERENCE TO RELATED APPLICATIONS

This is a continuation-in-part application that claims benefit under 35 U.S.C. 120 to Ser. No. 07/987,728 filed Dec. 9, 1992, now U.S. Pat. No. 5,472,907, contents of which are incorporated by reference.

BACKGROUND OF THE INVENTION

The present invention relates to an antipsychotic composition and to a method of treatment of patients suffering from serious psychotic mental illness.

Conventional antipsychotic drugs, termed "typical antipsychotics," are effective in improving symptoms of schizophrenia by acting as dopamine receptor antagonists, more particularly $D_2$ dopamine receptor antagonists, which also are known as $D_2$ dopamine receptor blockading agents. Such activity decreases the activity of the brain neurotransmitter dopamine. See Snyder, Am. J. Psychiatry 133: 197–202 (1976); Creese et al., Science 192:481–83 (1976); Seeman et al., Nature 251:717–19 (1976). Typical antipsychotics include those drugs known as "typical neuroleptics," exemplary of which are chlorpromazine, fluphenazine, trifluoperazine and haloperidol, among others. But a significant number of patients suffering from schizophrenia have proven resistant to treatment with typical neuroleptics.

It is known that clozapine, an "atypical neuroleptic," that is, an antipsychotic neuroleptic which produces few or no extrapyramidal side effects ("EPS's") and does not cause catalepsy in animal models, is effective in treating patients suffering from schizophrenia who had shown poor response to other drugs. Kane et al., Arch. Gen. Psychiatry 45:789–96 (1988). The mechanism of action of clozapine includes $\alpha_2$-adrenergic receptor antagonism, in addition to a dopamine-blockading action which is characteristic of typical antipsychotic neuroleptics. See Pickar et al., Arch. Gen. Psychiatry 49:345–53 (1992) ("Pickar et al.").

Use of clozapine is associated with severe side effects, however, including agranulocytosis, seizures and adverse cardiovascular effects. See, for example, THE PHYSICIANS' DESK REFERENCE (1992), pages 1942–45; Griffith et al., Lancet 2:657 (1979).

SUMMARY OF THE INVENTION

Accordingly, it is an object of the present invention to provide an effective method of treatment for patients suffering from serious psychotic mental illness who have not responded adequately to treatment with "typical" antipsychotics, such as antipsychotic neuroleptics.

It is another object of the present invention to provide a method of treatment which does not have the severe side effects associated with the administration of clozapine.

It is yet another object of the present invention to provide pharmaceutical compositions useful in the foregoing methods of treatment.

In accomplishing the foregoing objectives, there has been provided, in accordance with one aspect of the present invention, a method for treating a serious psychotic mental illness comprising the step of administering to a patient in need of such treatment a combination of (i) an $\alpha_2$-adrenergic receptor antagonist and (ii) a $D_2$ dopamine receptor antagonist. In a preferred embodiment, the $\alpha_2$-adrenergic receptor antagonist is idazoxan.

In accordance with another aspect of the present invention there is provided a pharmaceutical composition comprising a combination of (i) an $\alpha_2$-adrenergic receptor antagonist, (ii) a $D_2$ dopamine receptor antagonist, (iii) a pharmaceutically acceptable carrier, wherein the amount of ingredients (i) and (ii) is therapeutically effective against serious psychotic mental illness.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWING

The present invention can be understood more readily by reference to the accompanying drawing, by which:

FIG. 2 presents bar graphs which relate, respectively, BPRS negative (A) and positive (B) subscale values corresponding to treatment with fluphenazine prior to addition of idazoxan, with both compounds, and with fluphenazine after administration of idazoxan was discontinued. Asterisk (*): F(2,10)=3.50; p=0.07.

DETAILED DESCRIPTION OF PREFERRED EMBODIMENTS

Figure 1:
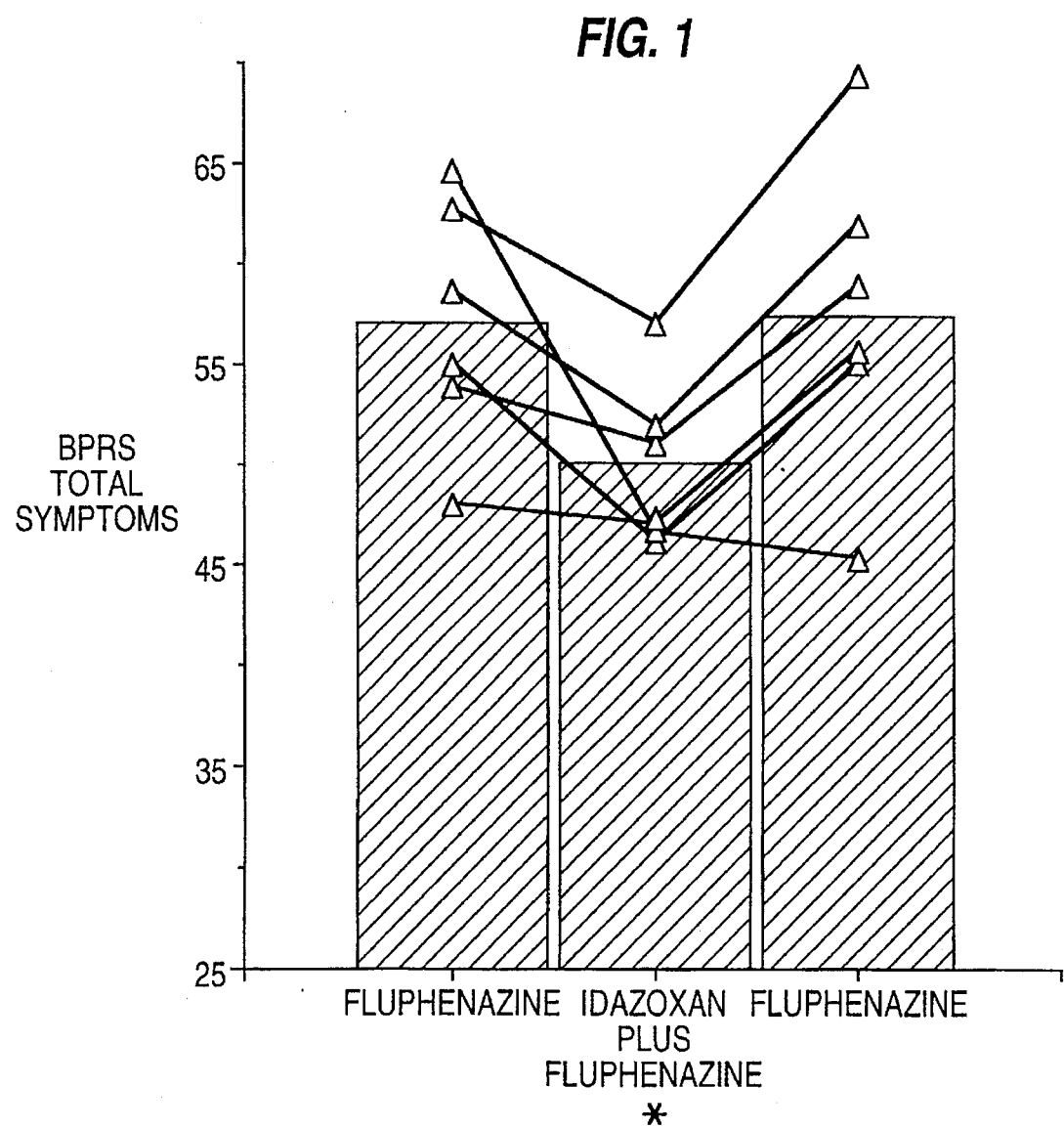
FIG. 1 is a bar graph that depicts total symptoms, measured in relation to the Brief Psychiatric Rating Scale (BPRS), in the context of treatment with fluphenazine, with fluphenazine plus idazoxan, and with fluphenazine after discontinuation of idazoxan. An asterisk (*) denotes a probability (p) <0.05 in a Duncan's Multiple Range post hoc test.

It has been discovered that the administration of an $\alpha_2$-adrenergic receptor antagonist unexpectedly enhances the therapeutic effect of typical antipsychotic neuroleptics. Thus, the combined administration of an $\alpha_2$-adrenergic receptor antagonist and a typical antipsychotic neuroleptic has been found to be an effective substitute for clozapine in treating patients suffering from serious psychotic mental illness. The present invention provides an improved treatment for patients suffering from serious psychotic mental illness who have proven resistant to treatments with known typical antipsychotic neuroleptics alone, which treatment is not characterized by the harmful side effects arising from treatment with clozapine.

The term "serious psychotic mental illness" denotes conditions in which delusions and/or hallucinations, along with other negative symptomatology, are present. See Diagnostic and Statistical Manual of Mental Disorders, 3rd rev'sd ed., 1993, ("DSM IIIR") and Diagnostic and Statistical Manual of Mental Disorders, 4th edition, 1994 ("DSM IV"), American Psychiatric Association, Committee on Nomenclature and Statistics (Washington, D.C., American); and Pickar et al.

Typical symptoms associated with serious psychotic mental illnesses include, inter alia, the sudden onset of delusions, or hallucinations, disorganized speech (e.g., frequent derailment or incoherence), grossly disorganized or catatonic behavior, paranoia, and major manic, depressive or mixed episodes. Illustrative of serious psychotic mental illnesses are schizophrenia and schizoaffective illnesses, brief psychotic disorders which involve the sudden onset of delusions, or hallucinations, disorganized speech (e.g. frequent derailment or incoherence), or grossly disorganized or catatonic behavior. Brief psychotic disorders are not schizoaffective disorders. Individuals experiencing brief psychotic disorders typically experience emotional turmoil or overwhelming confusion, may have rapid shifts from one intense affect to another, and typically exhibit poor judgement, cognitive impairment, or actions based upon delusions.

Within the context of the present invention, "serious psychotic mental illness" also includes Bipolar I disorders typically manifested by individuals who have previously experienced at least one manic episode or mixed episode and who later manifest a manic, hypomanic, mixed, or a major depressive episode which cause clinically significant distress or impairment in social, occupational or other important areas of functioning. The mood symptoms of Bipolar I disorders are not due to the direct physiological affects of substance abuse or medication and are not better accounted for by schizoaffective disorder and are not superimposed on schizophrenia, schizophreniform disorder, delusional disorder, or psychotic disorder not otherwise specified.

Serious psychotic mental illness pertains also to paranoid personality disorders wherein an individual manifests a pattern of pervasive distrust and suspiciousness of others such that the motives of others are interpreted as malevolent. Schizoid personality disorders and schizotypal personality disorders also fall within the parameters of the present invention. The essential feature of schizoid personality disorders is a pervasive pattern of detachment from social relationships and a restricted range of expression of emotions in interpersonal settings. Schizotype personality disorders manifest a pervasive pattern of social and interpersonal deficits marked by acute discomfort with, and reduced capacity for close relationships as well as by cognitive or perceptual distortions in eccentricities of behavior.

In sum, serious psychotic mental illnesses include, inter alia, Schizophreniform Disorder, Schizoaffective Disorder, Sever Schizoaffective Disorder with Psychotic Features, Bipolar I Disorders with a Single Manic Episode, Sever Bipolar I Disorders with Psychotic Features, Major Depressive Disorders Manifesting a Single Episode, Severe Major Depressive Disorders with Psychotic Features, Bipolar I Disorders Manifesting a Mixed Most Recent Episode, Severe Bipolar I Disorders with Psychotic Features, Brief Psychotic Disorders, Psychotic Disorders NOS, Paranoid Personality Disorders, Schizoid Personality Disorders, Schizophrenia, Schizotypal Personality Disorders with Sedative, Hypnotic, or Anxiolytic Manifestations, Major Depressive Disorders with Recurrent Episodes, and Psychotic Disorders due to Specific General Medical Conditions.

Preferably, the $\alpha_2$-adrenergic receptor antagonist utilized according to the invention is a selective antagonist, i.e., a drug whose principal pharmacological effect in vitro is antagonism of $\alpha_2$-adrenergic receptors. Any additional pharmacological effects should be minor in comparison to this principal effect.

A particularly preferred $\alpha_2$-adrenergic receptor antagonist for use according to the invention is idazoxan [(±)-2-(1,4-benzodioxan-2-yl)-2-imidazoline]. Idazoxan is a highly selective $\alpha_2$-adrenergic receptor antagonist. See Doxey et al., Arch. Pharmacol. 325:136–44 (1984). Other useful $\alpha_2$-adrenergic receptor antagonists include yohimbine, ethoxy-idazoxan, fluperoxan and atipamezole.

Non-limiting examples of antipsychotic neuroleptics useful according to the invention include thiopropazate, chlorpromazine, triflupromazine, mesoridazine, piperacetazine, thioridazine, acetophenazine, fluphenazine, perphenazine, trifluoperazine, chlorprathixene, thiothixene, haloperidol, bromperidol, loxapine and molindone.

In a preferred embodiment of the method according to the invention, the $\alpha_2$-adrenergic receptor antagonist is administered to a patient presently undergoing chronic neuroleptic treatment. This permits assessment of the effect of the neuroleptic prior to the administration of the $\alpha_2$-adrenergic receptor antagonist. The two compounds also can be administered together at the beginning of treatment, if desired.

Preferred dosages of the $\alpha_2$-adrenergic receptor antagonist according to the invention range from about 60 to 120 mg/day. Preferred dosages of the typical antipsychotic neuroleptic are routinely determined, and range from about 100 to about 900 mg/day chlorpromazine equivalents. See Snyder, supra, and Seeman, supra.

In one embodiment of the present invention, both the $\alpha_2$-adrenergic receptor antagonist and the antipsychotic neuroleptic can be administered in separate form. The two compounds can also be administered in a single pharmaceutical composition, in combination with known pharmaceutically acceptable carriers. Such pharmaceutical compositions thus constitute another aspect of the present invention. These compositions may be prepared from conventional materials by known procedures.

Compositions within the present invention can be adapted for oral or parenteral administration, as well as for enteral administration orally or through mucus membranes, that is, intranasally, sublingually, buccally or rectally.

Compositions for oral administration include capsules, tablets, dispersible powders, granules, syrups, elixirs and suspensions. These compositions can contain one or more conventional adjuvants, such as sweetening agents, flavoring agents, coloring agents and preserving agents.

Tablets can contain the active ingredients in a mixture with conventional pharmaceutically acceptable excipients. These include inert carriers, such as calcium carbonate, sodium carbonate, lactose, and talc; granulating and disintegrating agents, such as starch and alginic acid; binding agents such as starch, gelatin acacia; and lubricating agents, such as magnesium stearate, stearic acid and talc. Tablets may be uncoated or coated by known techniques to delay disintegration and absorption in the gastrointestinal tract thereby providing a sustained action over a longer period of time.

Capsules may contain the active ingredients alone or an admixture with an inert solid carrier, such as calcium carbonate, calcium phosphate or kaolin. Similarly, suspensions, syrups and elixirs may contain the active ingredients in mixture with any of the conventional excipients utilized in the preparation of such compositions. This includes suspending agents such as methylcellulose, tragacanth and sodium alginate; wetting agents such as lecithin, polyoxyethylene stearate or polyoxyethylene sorbitan monoleate; and preservatives.

The present invention is described further by reference to the following, illustrative examples.

EXAMPLE 1 Administration of Idazoxan in Combination with Fluphenazine

Six hospitalized patients (two female, four male) who met DSM-IIIR criteria for schizophrenia and had no medical or neurologic illness granted informed consent for a double-blind, placebo-controlled pharmacologic study during which idazoxan could be added to ongoing fluphenazine treatment. These patients also met criteria for treatment resistance to typical neuroleptics, to wit: (1) drug intolerance, defined as either significant tardive dyskinesia or EPSs, or (2) history of being refractory to treatment, defined as a lack of satisfactory clinical response to at least two different antipsychotic drugs given in adequate doses and for adequate periods.

Prior to treatment with idazoxan, patients were medicated with blinded capsules of fluphenazine hydrochloride (treatment duration: 56.5±17.4 days; mean daily dose: 27.9±11.4 mg) and placebo; patients were clinically stable on fluphenazine and placebo for at least four weeks prior to the addition of idazoxan, and no changes in fluphenazine dosage were made for at least four weeks prior to or during idazoxan treatment. Benztropine mesylate (in blinded capsules) was prescribed as indicated for EPSs; doses were unchanged for at least four weeks prior to the addition of idazoxan and throughout the study.

Idazoxan, also administered as blinded capsules, was started at an initial dose of 20 mg bid and increased by increments of 20 mg over two weeks to a maintenance dose of 120 mg/day. (One patient experienced one night of insomnia which responded rapidly to dosage adjustment of idazoxan; this patient was maintained instead of 100 mg/day for the study duration.)

All patients were treated with idazoxan at maintenance doses for 4–6 weeks (32.6±11.4 days). Idazoxan was then tapered by reductions of 20 mg/day over two weeks. Following discontinuation of idazoxan, patients were studied for three additional weeks (23.2±6.3 days) on fluphenazine. All medications were administered under double blind conditions. Patients received placebo capsules which were identical in appearance to blinded idazoxan and fluphenazine capsules before, during and after idazoxan treatment.

Physicians who were blind to medication phase and who had no knowledge regarding the initiation and discontinuation of idazoxan treatment completed both the Brief Psychiatric Rating Scale, defined in Overall et al., Psychol. Rep. 10:799–812 (1961), and the Simpson Neurological Rating Scale, defined in Simpson et al., Acta Psychiatr. Scand. 212 (suppl'mt): 9–11 (1970), for drug side effects weekly for all patients. Additionally, blood samples were collected for plasma fluphenazine levels from five of six patients via standard venipuncture at 7:30 a.m. following overnight fast, during treatment with fluphenazine before addition of idazoxan, and during combined treatment with fluphenazine and idazoxan, after at least two weeks of stable medication doses.

Rating scale total scores were averaged from the three weeks immediately preceding idazoxan treatment, the last four weeks of maintenance idazoxan treatment, and the three weeks immediately following idazoxan discontinuation for each patient. Differences in rating scores were analyzed as indicated in Table 1 and FIGS. 1–2.

As is apparent from Table 1 and from FIG. 1, combined administration of idazoxan and fluphenazine resulted in significant decreases in mean BPRS total score when compared to fluphenazine treatment alone, both before and after addition of idazoxan. Negative symptoms measured by the BPRS negative symptoms subscale were similarly reduced by the idazoxan-fluphenazine combination, to a degree which approached statistical significance (Table 1 and FIG. 2A). Differences in positive symptoms as measured by the BPRS positive symptoms subscale were not statistically significant (Table 1); however, three out of six patients showed clinically significant reductions in positive symptoms (FIG. 2B). Adding idazoxan to fluphenazine did not result in significant changes in extrapyramidal symptoms as measured by the Simpson Neurological Rating Scale, nor did it result in increases in plasma fluphenazine levels (mean plasma fluphenazine without idazoxan: 1.66±0.56 ng/ml; with idazoxan: 1.80±0.74 ng/ml; T=−0.5, df=4, p<0.7). With the exception of one patient who experienced transient insomnia, idazoxan was well tolerated by patients, who experienced no clinically significant side effects.

Thus, it is apparent that the addition of idazoxan to typical neuroleptic therapy can improve treatment response in treatment-resistant patients suffering from schizophrenia. All six patients showed some improvement in symptoms with the addition of idazoxan, and five had worsening of symptoms upon idazoxan discontinuation. The most significant improvement occurred in the negative symptoms subscale of the BPRS, although improvement in positive symptoms occurred in three of the patients studied. The reduction in BPRS total score observed with idazoxan treatment is comparable to the reduction in BPRS total score of a similar group of patients treated for a comparable time period with moderate doses of clozapine [see Pickar et al., supra].

EXAMPLE 2 Formulations

Pharmaceutical compositions according to the present invention can include the $\alpha_2$-adrenergic receptor antagonist and the $D_2$ dopamine receptor antagonist in various proportions. For example, a tablet can include trifluoperazine and idazoxan in the proportions 5 mg: 40–80 mg. A capsule can include chlorpromazine and idazoxan in the proportions 100–200 mg: 40 mg.

What is claimed is:

1. A method for treating a serious psychotic mental illness comprising the step of administering to a patient in need of such treatment a therapeutically effective amount of a combination of (i) an $\alpha_2$-adrenergic receptor antagonist and (ii) a $D_2$ dopamine receptor antagonist in a pharmaceutically acceptable carrier.

2. A method as claimed in claim 1, wherein said $\alpha_2$-adrenergic receptor antagonist (i) is selected from the group consisting of idazoxan, yohimbine, ethoxy-idazoxan, fluperoxan and atipamezole.

3. A method as claimed in claim 2 wherein said $\alpha_2$-adrenergic receptor antagonist (i) is idazoxan.

TABLE 1

Behavioral Ratings During Fluphenazine Treatment, Combined Idazoxan and Fluphenazine Treatment, and Fluphenazine Treatment After Discontinuation of Idazoxan (N = 6)[a]

| Rating Scale | Fluphenazine[b] | Idazoxan and Fluphenazine | Fluphenazine[c] | Repeated Measures ANOVA F | P |
|---|---|---|---|---|---|
| BPRS total | 57.4 + 6.2 | 50.3 + 4.2* | 58.1 + 8.0 | 4.16 | 0.05 |
| BPRS positive symptoms | 8.5 + 3.2 | 7.4 + 1.9 | 9.3 + 1.4 | 1.22 | 0.33 |
| BPRS negative symptoms | 10.7 + 2.4 | 9.4 + 1.7 | 10.6 + 2.0 | 3.50 | 0.07 |
| SNS total | 12.9 + 1.6 | 12.2 + 1.2 | 12.9 + 1.5 | 1.33 | 0.30 |

[a]BPRS indicates Brief Psychiatric Rating Scale; SNS, Simpson Neurological Scale; ANOVA, Analysis of Variance, Values are expressed as mean + SD; df = 2,10 for all comparisons.
[b]prior to addition of idazoxan
[c]after discontinuation of idazoxan
*p < 0.05 vs fluphenazine treatment before the addition and after discontinuation of idazoxan, Duncan's Multiple Range Test 4. A method as claimed in claim 1, wherein said $D_2$ dopamine receptor antagonist (ii) is an antipsychotic neuroleptic drug.

5. A method as claimed in claim 4, wherein said antipsychotic neuroleptic drug is selected from the group consisting of thiopropazate, chlorpromazine, triflupromazine, mesoridazine, piperacetazine, thioridazine, acetophenazine, fluphenazine, perphenazine, trifluoperazine, chlorprathixene, thiothixene, haloperidol, bromperidol, loxapine, and molindone.

6. A method as claimed in claim 1, wherein said $\alpha_2$-adrenergic receptor antagonist (i) is administered in an amount from about 60 to 120 mg/day.

7. A method as claimed in claim 1, wherein said serious psychotic mental illness is schizoprenia.

8. A pharmaceutical composition comprising a combination of (i) an $\alpha_2$-adrenergic receptor antagonist, (ii) a $D_2$ dopamine receptor antagonist, and (iii) a pharmaceutically acceptable carrier, wherein the amount of said ingredients (i) and (ii) is therapeutically effective against serious psychotic mental illness.

9. A composition as claimed in claim 8, wherein said $\alpha_2$-adrenergic receptor antagonist (i) is selected from the group consisting of idazoxan, yohimbine, ethoxy-idazoxan, fluperoxan and atipamezole.

10. A composition as claimed in claim 9, wherein said $\alpha_2$-adrenergic receptor antagonist (i) is idazoxan.

11. A composition as claimed in claim 8, wherein said $D_2$ dopamine receptor antagonist (ii) is an antipsychotic neuroleptic drug.

12. A composition as claimed in claim 11, wherein said antipsychotic neuroleptic drug is selected from the group consisting of thiopropazate, chlorpromazine, triflupromazine, mesoridazine, piperacetazine, thioridazine, acetophenazine, fluphenazine, perphenazine, trifluoperazine, chlorprathixene, thiothixene, haloperidol, bromperidol, loxapine, and molindone.

13. A method for treating a serious psychotic mental illness comprising the step of administering to a patient in need of such treatment a therapeutically effective amount of a combination of (i) an $\alpha_2$-adrenergic receptor antagonist and (ii) a $D_2$ dopamine receptor antagonist in a pharmaceutically acceptable carrier, wherein said serious psychotic mental illness is selected from the group consisting of Schizophreniform Disorder, Severe Schizoaffective Disorder with Psychotic Features, Bipolar I Disorders with a Single Manic Episode, Severe Bipolar I Disorders with Psychotic Features, Major Depressive Disorders Manifesting a Single Episode, Severe Major Depressive Disorders with Psychotic Features, Bipolar I Disorders Manifesting a Mixed Most Recent Episode, Severe Bipolar I Disorders with Psychotic Features, Brief Psychotic Disorders, Psychotic Disorders NOS, Paranoid Personality Disorders, Schizoid Personality Disorders, Schizotypal Personality Disorders with Sedative, Hypnotic, or Anxiolytic Manifestations, Major Depressive Disorders with Recurrent Episodes, and Psychotic Disorders due to Specific General Medical Conditions.

14. The method as claimed in claim 13, whereto said $\alpha_2$-adrenergic receptor antagonist (i) is one or more selected from the group consisting of idazoxan, yohimbine, ethoxy-idazoxan, fluperoxan and atipamezole, and wherein said $D_2$ dopamine receptor antagonist (ii) is one or more selected from the group consisting of thiopropazate, chlorpromazine, triflupromazine, mesoridazine, piperacetazine, thioridazine, acetophenazine, fluphenazine, perphenazine, trifluoperazine, chlorprathixene, thiothixene, haloperidol, bromperidol, loxapine, and molindone.

15. The method as claimed in claim 13, wherein said $\alpha_2$-adrenergic receptor antagonist (i) is administered in an amount from about 60 to 120 mg/day.

\* \* \* \* \*